United States Patent
Wu

(10) Patent No.: US 8,973,748 B2
(45) Date of Patent: Mar. 10, 2015

(54) MEDICAL DEVICE PACKAGING AND METHODS FOR PREPARING AND PACKAGING MEDICAL DEVICES

(75) Inventor: Maan-Shii Wu, Mendota Heights, MN (US)

(73) Assignee: Boston Scientific Scime, Inc., Maple Grove, MN (US)

( * ) Notice: Subject to any disclaimer, the term of this patent is extended or adjusted under 35 U.S.C. 154(b) by 399 days.

(21) Appl. No.: 13/354,261

(22) Filed: Jan. 19, 2012

(65) Prior Publication Data

US 2012/0187002 A1 Jul. 26, 2012

Related U.S. Application Data

(60) Provisional application No. 61/434,244, filed on Jan. 19, 2011.

(51) Int. Cl.
| | | |
|---|---|---|
| *B65D 81/26* | (2006.01) | |
| *B29D 22/00* | (2006.01) | |
| *A61F 2/00* | (2006.01) | |
| *A61M 25/00* | (2006.01) | |

(Continued)

(52) U.S. Cl.
CPC ............ *A61F 2/0095* (2013.01); *A61M 25/002* (2013.01); *B65D 31/12* (2013.01); *B65D 81/2084* (2013.01); *A61F 2/95* (2013.01); *A61F 2210/0076* (2013.01)
USPC ....... 206/204; 206/438; 206/484.2; 428/35.2; 428/35.9

(58) Field of Classification Search
USPC .............. 206/204, 207, 210, 213.1, 363, 438, 206/484, 484.2; 428/35.2, 35.5, 35.7, 35.9, 428/36.91
See application file for complete search history.

(56) References Cited

U.S. PATENT DOCUMENTS 3,754,700 A 8/1973 Bonk
3,815,315 A * 6/1974 Glick ........................... 206/210
(Continued)

FOREIGN PATENT DOCUMENTS

EP 0492399 A2 7/1992
EP 0629415 A1 12/1994
(Continued)

OTHER PUBLICATIONS

"Tekni-Films Instroduces Tekniflex® Modified Atmosphere Blister (MAB) Package," Article from http://www.tekni-films.com website, Mar. 29, 2006.

*Primary Examiner* — Luan K Bui
(74) *Attorney, Agent, or Firm* — Seager, Tufte & Wickhem, LLC

(57) ABSTRACT

Medical device packaging, medical device packaging assemblies, and methods for preparing and packaging medical devices. An example medical device packaging assembly may include a packaging pouch including a front pouch portion and a back pouch portion. The front pouch portion may include a first sheet of material having a plurality of layers. The back pouch portion may include a second sheet of material having a plurality of layers. A medical device may be disposed in the pouch. At least one of the plurality of layers of first sheet of material and the plurality of layers of second sheet of material may include a moisture scavenging layer. In addition, at least one of the plurality of layers of first sheet of material and the plurality of layers of second sheet of material may include a barrier layer that is configured to maintain the oxygen concentration within the packaging pouch.

12 Claims, 6 Drawing Sheets

(51) Int. Cl.
  *B65D 30/22* (2006.01)
  *B65D 81/20* (2006.01)
  *A61F 2/95* (2013.01)

(56) References Cited

U.S. PATENT DOCUMENTS

| | | | |
|---|---|---|---|
| 3,851,814 A | 12/1974 | Stage | |
| 3,926,311 A | 12/1975 | Laske | |
| 3,942,634 A * | 3/1976 | Gandi et al. | 206/210 |
| 4,154,342 A | 5/1979 | Wallace | |
| 4,216,860 A | 8/1980 | Heimann | |
| 4,730,726 A | 3/1988 | Holzwarth | |
| 4,861,632 A * | 8/1989 | Caggiano | 428/35.2 |
| 4,941,308 A | 7/1990 | Grabenkort et al. | |
| 5,217,114 A | 6/1993 | Gadberry et al. | |
| 5,577,368 A | 11/1996 | Hamilton et al. | |
| 5,590,778 A | 1/1997 | Dutchik | |
| 5,620,656 A | 4/1997 | Wensky et al. | |
| 5,681,322 A | 10/1997 | Hartigan, Jr. | |
| 5,690,623 A | 11/1997 | Lenz | |
| 5,730,150 A | 3/1998 | Peppel et al. | |
| 5,848,691 A | 12/1998 | Morris et al. | |
| 5,874,045 A | 2/1999 | Chisum | |
| 5,928,516 A | 7/1999 | Hopkins et al. | |
| 5,935,501 A | 8/1999 | Andrews et al. | |
| 6,065,597 A | 5/2000 | Pettersson et al. | |
| 6,174,934 B1 | 1/2001 | Sun | |
| 6,312,646 B2 | 11/2001 | Kowanko | |
| 6,423,226 B1 | 7/2002 | Hopkins et al. | |
| 6,585,702 B1 | 7/2003 | Brunel | |
| 6,871,740 B1 | 3/2005 | Cao | |
| 6,875,400 B2 | 4/2005 | Speer | |
| 6,991,095 B1 * | 1/2006 | Yamasoto et al. | 206/204 |
| 7,000,770 B2 | 2/2006 | Clarke | |
| 7,040,485 B2 | 5/2006 | Gupta | |
| 7,108,682 B2 | 9/2006 | Duffy et al. | |
| 7,178,555 B2 | 2/2007 | Engel | |
| 7,211,308 B2 | 5/2007 | Rhee | |
| 7,234,597 B2 | 6/2007 | Rowe et al. | |
| 7,261,205 B2 | 8/2007 | Cervantes | |
| 7,303,734 B2 | 12/2007 | Moriyama | |
| 7,337,593 B2 | 3/2008 | Blum | |
| 7,353,946 B2 | 4/2008 | Cervantes | |
| 7,631,760 B2 | 12/2009 | Guelzow et al. | |
| 7,694,810 B1 | 4/2010 | Barry et al. | |
| 7,694,813 B2 | 4/2010 | Shalaby | |
| 7,762,044 B2 * | 7/2010 | Clarke et al. | 53/403 |
| 7,776,003 B2 | 8/2010 | Zauner | |
| 7,909,249 B2 | 3/2011 | Bagozzi et al. | |
| 8,235,209 B2 * | 8/2012 | Peck et al. | 206/364 |
| 2002/0015673 A1 | 2/2002 | Moriyama | |
| 2003/0008152 A1 | 1/2003 | Tsai | |
| 2003/0178329 A1 | 9/2003 | Furukawa | |
| 2004/155053 A1 | 8/2004 | Sanchez | |
| 2004/0187438 A1 | 9/2004 | Clarke | |
| 2004/0243214 A1 | 12/2004 | Farrell | |
| 2005/0109648 A1 | 5/2005 | Kerzman et al. | |
| 2005/0143803 A1 | 6/2005 | Watson | |
| 2005/0199521 A1 | 9/2005 | Givens | |
| 2005/0218022 A1 | 10/2005 | Cervantes | |
| 2005/0278012 A1 | 12/2005 | Vonderwalde | |
| 2006/0016708 A1 * | 1/2006 | Ingraham | 206/439 |
| 2006/0086254 A1 | 4/2006 | Fudge et al. | |
| 2006/0260967 A1 * | 11/2006 | Clarke et al. | 206/438 |
| 2007/0014951 A1 | 1/2007 | Soerensen et al. | |
| 2007/0084144 A1 | 4/2007 | Labrecque et al. | |
| 2007/0092167 A1 | 4/2007 | Tilman et al. | |
| 2007/0158227 A1 * | 7/2007 | Amano et al. | 206/438 |
| 2007/0160789 A1 * | 7/2007 | Merical et al. | 428/35.7 |
| 2009/0269444 A1 | 10/2009 | Thomas, Jr. | |
| 2009/0314676 A1 | 12/2009 | Peck et al. | |
| 2011/0079525 A1 * | 4/2011 | Peck et al. | 206/438 |
| 2012/0037525 A1 | 2/2012 | Peck et al. | |

FOREIGN PATENT DOCUMENTS

| | | |
|---|---|---|
| EP | 0782868 A1 | 7/1997 |
| EP | 0944474 B1 | 10/2002 |
| WO | WO 9903754 A1 | 1/1999 |
| WO | WO 2004066876 A1 | 8/2004 |
| WO | WO 2004071308 A1 | 8/2004 |
| WO | WO 2005058586 A2 | 6/2005 |

* cited by examiner

US 8,973,748 B2

MEDICAL DEVICE PACKAGING AND METHODS FOR PREPARING AND PACKAGING MEDICAL DEVICES

CROSS-REFERENCE TO RELATED APPLICATION

This application claims the benefit of U.S. Provisional Application Ser. No. 61/434,244, filed Jan. 19, 2011, the entire disclosure of which is incorporated herein by reference.

TECHNICAL FIELD

The present invention pertains to medical devices, medical device packaging, and methods for preparing and packaging medical devices. More particularly, the present invention pertains to medical device packages that include both moisture scavenging and oxygen level maintaining capabilities.

BACKGROUND

A wide variety of intracorporeal medical devices have been developed for medical use, for example, intravascular use. Some of these devices include guidewires, catheters, and the like. These devices are manufactured, packaged, and/or prepared by any one of a variety of methods. Of the known medical devices and methods, each has certain advantages and disadvantages. There is an ongoing need to provide alternative medical devices as well as alternative methods for manufacturing, packaging, and/or preparing medical devices.

BRIEF SUMMARY

Embodiments of the present disclosure provide design, material, and use alternatives for medical device packaging and packaging assemblies, as well as methods for preparing and packaging medical devices. An example medical device packaging assembly may include a packaging pouch including a front pouch portion and a back pouch portion. The front pouch portion may include a first sheet of material having a plurality of layers. The back pouch portion may include a second sheet of material having a plurality of layers. A medical device may be disposed in the pouch. At least one of the plurality of layers of first sheet of material and the plurality of layers of second sheet of material may include a moisture scavenging layer. In addition, at least one of the first sheet of material and the second sheet of material may include a barrier layer that is configured to maintain the oxygen concentration within the packaging pouch.

Another example medical device packaging assembly may include a packaging pouch having a front pouch portion and a back pouch portion. Each of the front pouch portion and the back pouch portion may include a plurality of layers. A medical device may be disposed in the pouch. The front pouch portion may include an oxygen maintaining layer that is configured to maintain the oxygen concentration within the packaging pouch. The back pouch portion may include a moisture scavenging layer.

An example method for packaging a medical device may include providing a packaging pouch including a front pouch portion and a back pouch portion. Each of the front pouch portion and the back pouch portion may include a plurality of layers. The front pouch portion may include an oxygen maintaining layer that is configured to maintain the oxygen concentration within the packaging pouch. The back pouch portion may include a moisture scavenging layer. The method may also include disposing a medical device disposed in the pouch and sealing the packaging pouch.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

Embodiments of the present disclosure may be more completely understood in consideration of the following detailed description in connection with the accompanying drawings, in which.

Figure 1:
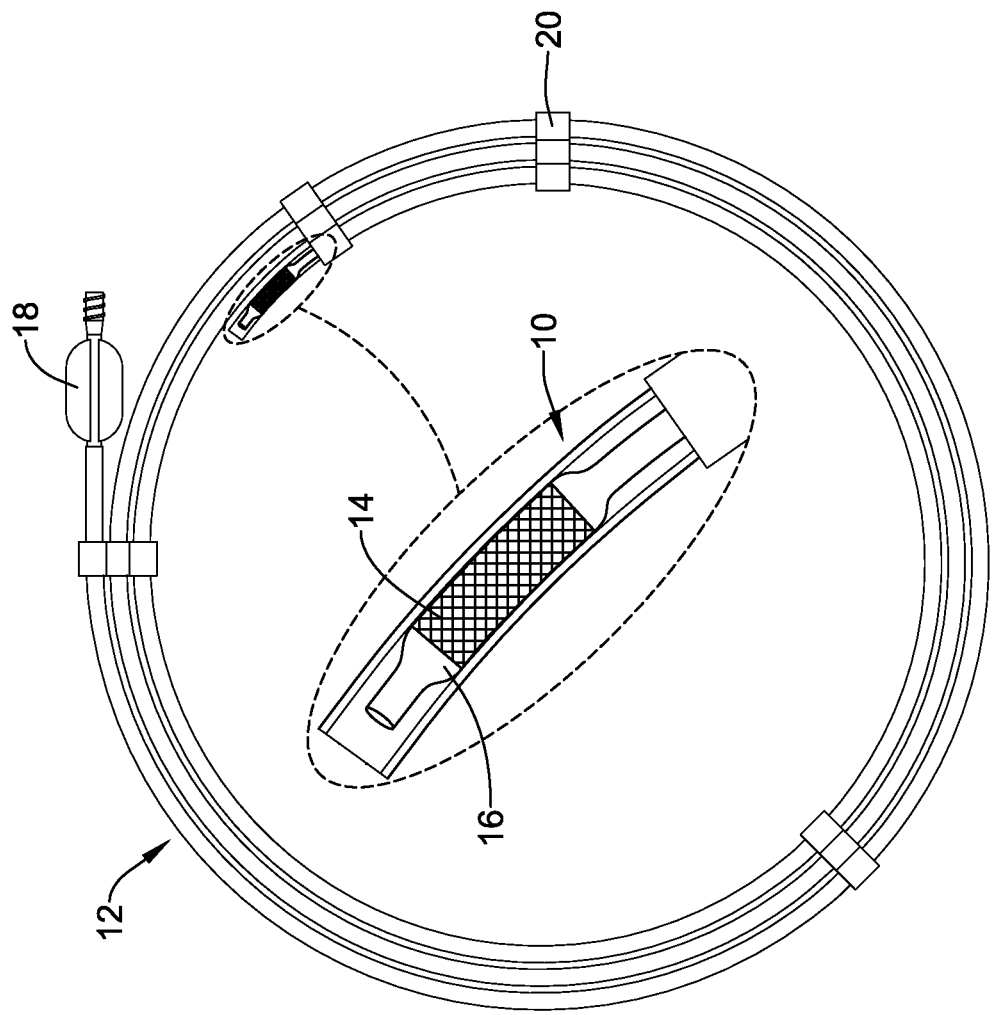
FIG. 1 is a side view of an example medical device disposed within a carrier tube.

While embodiments described herein are is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

For obvious reasons, medical devices are typically sterilized or otherwise prepared for use prior to sale. In order to preserve sterility, medical devices are usually contained within appropriate packaging that allows the sterile medical devices to be shipped to and stored by the purchaser. For example, prior to sale, medical devices such as catheters are typically sterilized and packaged. When suitably prepared, the catheters can be transported to an appropriate medical setting where they can be stored until needed for use.

Once packaged, it may be desirable to limit that exposure of a number of medical devices to particular substances and/or conditions. For example, it may be desirable to reduce moisture and/or oxygen exposure of medical devices. This may be particularly relevant when the medical device includes a material that may be adversely affected by exposure to oxygen and/or moisture. For example, some medical devices may include a drug-coated stent that can swell or otherwise be altered if exposed to oxygen and/or moisture. Therefore, packaging that includes a suitable barrier to moisture and/or oxygen may improve the storage conditions for a medical device and may improve the shelf life of the device.

Additionally, it may be desirable for at least a portion of a medical device package to be sufficiently transparent. This may also a clinician to visualize the product to, for example, verify that it is the proper product for the intended intervention as well as in order to verify the integrity of the device.

Disclosed herein are a number of medical device packages and/or packaging components, methods for packaging and/or preparing a medical device for sale, and methods for improving the shelf life of medical devices. In at least some embodiments, the packages, packaging components, and methods provide a suitable barrier to moisture and/or oxygen. In addition, at least some of the packages and packaging components disclosed herein include both a moisture scavenging layer or portion and another layer or portion that is configured to control and/or maintain oxygen levels within the package. This may further reduce the amount of exposure to moisture and/or oxygen that a medical device disposed in these packages may experience. Furthermore, medical device packaging is also disclosed that includes at least a portion that is sufficiently transparent. Other features and benefits are also disclosed, as discussed herein.

FIG. 1 illustrates an example medical device 10 disposed within a carrier tube 12. In this example, medical device 10 may include a catheter for delivery of an endoprosthesis. For example, medical device 10 may include an endoprosthesis or stent 14 attached thereto. In some embodiments, stent 14 is disposed on a balloon 16, which may be used to expand stent 14. In other embodiments, stent 14 is a self-expanding stent and, as such, medical device 10 may be a catheter suitable for delivery thereof. In either embodiment, stent 14 may be a bare metal stent or may include one or more substances associated therewith such as pharmaceuticals or the like (e.g., stent 14 may be a drug-coated or drug-eluting stent). Medical device 10 may also include a proximal hub 18. It can be appreciated that medical device 10 may differ vastly in form and can include any other suitable medical devices including catheters, guidewires, or the like.

Carrier tube 12 may generally be configured to hold medical device 10 in a suitable configuration. In at least some embodiments, carrier tube 12 may be arranged or otherwise configured as a coil that allows medical device 10, which may have a reasonably long length, to be held in a compact configuration. The individual windings of the coil may be secured together by one or more clips 20 as is typical in the art. Other configurations for carrier tube 12 include configurations suitable for holding other medical devices.

Figure 2:
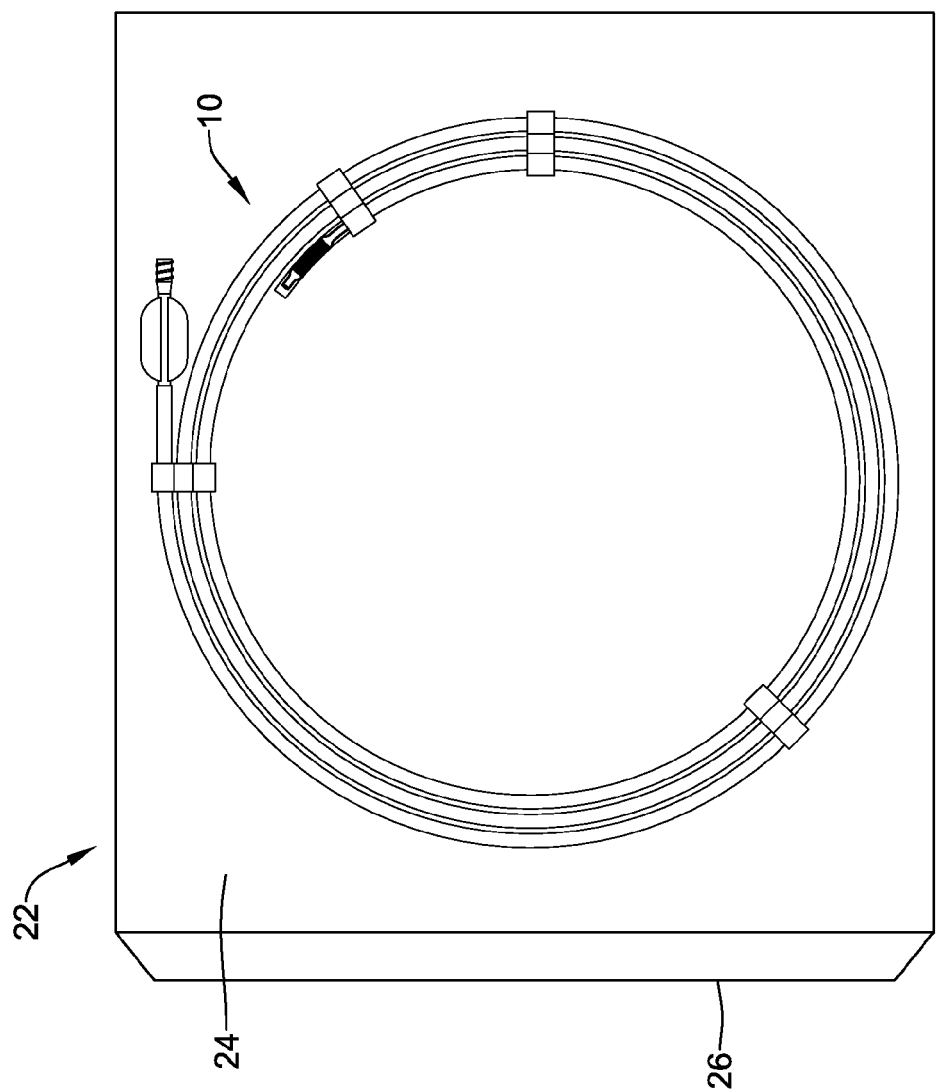
FIG. 2 is a side view of the example medical device shown in FIG. 1 disposed within an example medical device package.

FIG. 2 illustrates medical device 10 disposed in a medical device package or packaging assembly 22. In general, package 22 may take the form of a pouch that includes a first or "front" portion 24 and a second or "back" portion 26. In at least some embodiments, at least one of first portion 24 and second portion 26 is substantially transparent so as to allow a clinician to visualize medical device 10 while device 10 is within package 22.

In at least some embodiments, package 22 may be designed so as to not only be a suitable barrier to moisture and/or oxygen ingress, package 22 may also include one or more moisture scavenging and/or oxygen level maintaining portions or layers. For example, first portion 24 may include a barrier film capable of maintaining oxygen levels within package 22 and second portion 26 may include a moisture scavenging layer (e.g., layer 38, which is described in more detail below). The combination of both an oxygen maintaining layer and a moisture scavenging layer may be desirable for a number of reasons. For example, package 22 may include a medical device that may be (or include one or more components that may be) adversely affected by exposure to oxygen and/or moisture. Therefore, reducing the exposure of the device to moisture and/or oxygen may improve the storage conditions for the medical device and may improve the shelf life of the device.

In at least some embodiments, package 22 may be considered a "primary" pouch in that medical device 10 may be disposed directly within package 22. In some of these embodiments, package 22 may be the entire structure between medical device 10 and the exterior environment. In other embodiments, a secondary pouch or package (not shown) may be disposed about package 22. In still further alternative embodiments, medical device 10 may be disposed in another primary pouch and package 22 may be considered a secondary pouch.

In some embodiments, first and second portions 24/26 may be formed of a layer or film of material, which may or may not be the same material. Alternatively, first and second portions 24/26 may include a plurality of layers. For example, first and/or second portions 24/26 may include two, three, four, five, six, seven, eight, nine, ten, eleven, twelve, or more layers. The number and/or make-up of the layers may or may not be the same for portions 24/26 and can vary.

Figure 3:
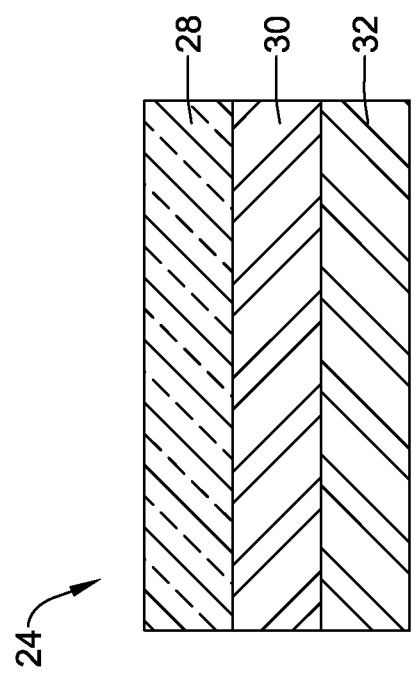
FIG. 3 is a cross-sectional view depicting a first portion of the example medical device package having plurality of layers.

FIG. 3 illustrates an example cross-section of first portion 24. In this example, first portion 24 includes three layers including first layer 28, second layer 30, and third layer 32. Other embodiments are contemplated, however, where first portion 24 includes more or less than three layers. In the embodiment illustrated in FIG. 3, first layer 28 may be understood to be the "inner" layer of first portion 24. Thus, first layer 28 may generally face medical device 10 when device 10 is within package 22. Likewise, third layer 32 may be understood to be the "outer" layer of first portion 24 and, thus, may face the external environment.

In some embodiments, layer 28 may be a sealant layer including materials such as, for example, ethylene-based homopolymers or copolymers. For example, layer 28 may include medium-density polyethylene, low-density polyethylene (for example MARLEX® low-density polyethylene), linear low density polyethylene (for example REXELL®), ionomer, ethylene vinyl acetate (EVA) and/or copolymers thereof, ethylene methacrylate (EMA), ethylene acrylic acid (EAA), ethylene methacrylic acid (EMAA), blends and/or copolymers thereof, or the like, or any other suitable material. In some embodiments, layer 28 may be designed to be peelable. In such embodiments, for example, layer 28 may include a blend of one of the above materials with a polybutene resin. Alternatively, layer 28 may include a modified EVA or EMA copolymer. For example, layer 28 may include APPEEL® resin, which is commercially available from DuPont. These are just examples. Other polymers are contemplated including any of those disclosed herein.

Layer 30 may be a tie layer that is disposed adjacent layer 28 and, thus, may tie or join together layers 28/32. Tie layer 30 may include a lamination adhesive, an extrusion adhesive, or the like. A suitable lamination adhesive may be a two-part moisture-cured solvent-borne polyurethane such as ADCOTE®, which is commercially available from Dow Chemical. In extrusion lamination, those resins used in the co-extrusion field may be equally applicable as the adhesive. For example, anhydride- or acid-modified ethylene-based homopolymers or compolymers may be used such as medium-density polyethylene, low-density polyethylene (for example MARLEX® low-density polyethylene), linear low density polyethylene (for example REXELL®), high-density polyethylene (for example MARLEX® high-density polyethylene), ethylene acrylates such as BYNEL® (available from DuPont), blends and/or copolymers thereof, or the like, or any other suitable material may be used as an extrusion adhesive. Other materials are contemplated.

Layer 32 may include a number of different materials and/or films. For example, layer 32 may include a polyethylene terephthalate and/or a polyethylene terephthalate film. In some embodiments, layer 32 may include a coated polyethylene terephthalate film. For example, layer 32 may include an aluminum oxide (e.g., $AlO_x$) coated polyethylene terephthalate film, a silicon oxide (e.g., $SiO_x$) coated polyethylene terephthalate film, or the like. The coated polyethylene terephthalate film may be desirable for a number of reasons. For example, the coated polyethylene terephthalate film may provide a high barrier to both moisture and oxygen. Thus, layer 32 may be termed a "barrier" layer.

In some embodiments, layer 32 may include two or more layers of, for example, an aluminum oxide (e.g., $AlO_x$) coated polyethylene terephthalate film and/or an silicon oxide (e.g., $SiO_x$) coated polyethylene terephthalate film with a suitable tie resin therebetween taking the form of a laminated structures. In still other embodiments, layer 32 may be a laminate of polyethylene terephthalate film with a high-barrier film such as a polychlorotrifluoroethylene material (e.g., ACLAR® film commercially available from Honeywell). Such a laminate may be suitable barrier to moisture and/or oxygen and may be formed using typical adhesive laminating processes.

In one example embodiment, layer 32 may include an aluminum oxide (e.g., $AlO_x$) coated polyethylene terephthalate film, a 2-part polyurethane adhesive, and a linear low density polyethylene (LLDPE) film. In another example embodiment, layer 32 may include a polyethylene terephthalate film, an adhesive (e.g., 2-part polyurethane adhesive), a polychlorotrifluoroethylene film (e.g., ACLAR® film, commercially available from Honeywell), an adhesive (e.g., 2-part polyurethane adhesive), and a LLDPE film. In another example embodiment, layer 32 may include an aluminum oxide coated polyethylene terephthalate film, a 2-part polyurethane adhesive, another aluminum oxide coated polyethylene terephthalate film, and a LLDPE film. These are just examples.

The polyethylene terephthalate film may be a biaxially oriented film having a thickness of about 1 to 100 micrometers, or about 10 to 20 micrometers, or about 12-13 micrometers. The coating on the polyethylene terephthalate film may be deposited thereon via any suitable process. In at least some embodiments, the coating on the polyethylene terephthalate film may be deposited via a chemical vapor deposition. This may result in a coating having a thickness of about 0.1 to 100 nanometers, or about 0.5 to 2 nanometers, or about 1 nanometer being deposited on the polyethylene terephthalate film. These are just examples.

In at least some embodiments, layer 32 may be configured to be a suitable barrier to oxygen. For example, layer 32 may be configured to maintain levels of oxygen within package 22 at or below about 0.5% (e.g., at or below about 5000 ppm, oxygen), at or below about 0.4%, at or below about 0.3%, or at or below about 0.2%. Such levels may be maintained for a prolonged period of time. For example, layer 32 may be configured to maintain levels of oxygen within package 22 at or below about 0.5%, at or below about 0.4%, at or below about 0.3%, or at or below about 0.2% for about 152 days or more, for about 152 days, or about 150 day or more, or about 126 days or more, or about 120 days or more, or about 92 days or more, or about 90 days or more, or about 62 days or more, or about 60 days or more, or about 33 days or more, or about 30 days or more, or about 14 days or more.

In some embodiments, another layer or coating may be disposed on barrier layer 32. Such a coating may be a flexible coating disposed on top of the oxide coating in order to protect it from cracking during handling. In these and/or other embodiments, a second barrier layer may also be used and this additional barrier layer may be laminated with barrier layer 32 using any suitable tie layer or resin including those disclosed herein. This may further enhance the oxygen and moisture resistance to package 22.

Collectively, layers 28/30/32 may all be sufficiently transparent so that a clinician may view medical device 10 through first portion 24 and be able to visualize medical device 10.

Figure 4:
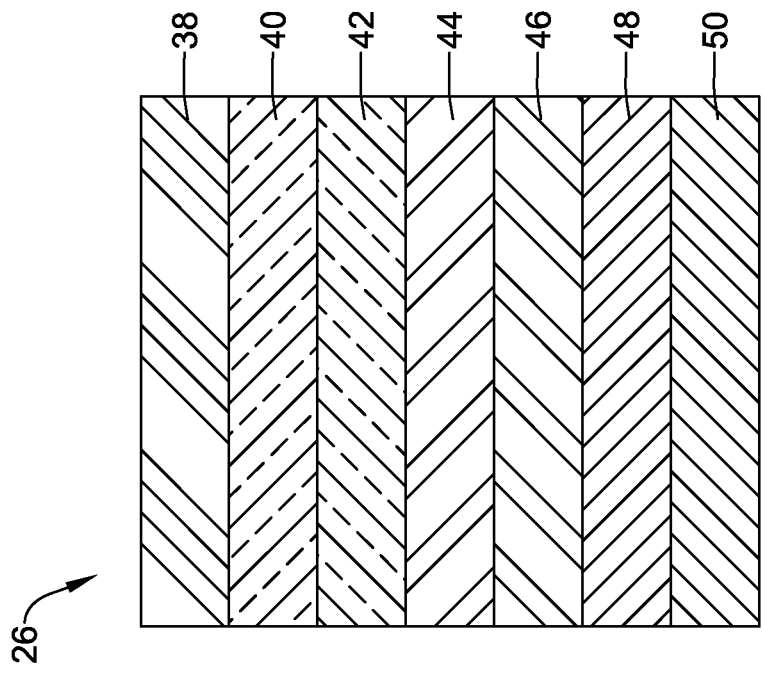
FIG. 4 is a cross-sectional view depicting a second portion of the example medical device package having plurality of layers.

In some embodiments, second portion 26 may be the same as first portion 24. Thus, both first portion 24 and second portion 26 may be sufficiently transparent. However, in other embodiments, second portion 26 may be substantially opaque. FIG. 4 illustrates an example cross-section of second portion 26. In this example, second portion 26 is different from first portion 24 and includes seven layers including first layer 38, second layer 40, third layer 42, fourth layer 44, fifth layer 46, sixth layer 48, and seventh layer 50. Other embodiments are contemplated, however, where second portion 26 includes more or less than seven layer. In the embodiment illustrated in FIG. 4, first layer 38 may be understood to be the "inner" layer of second portion 26. Thus, first layer 38 may generally face medical device 10 when device 10 is within package 22. Likewise, seventh layer 50 may be understood to be the "outer" layer of second portion 26 and, thus, may face the external environment.

In some embodiments, layer 38 may be a sealant layer including materials similar to layer 28. For example, layer 38 may include ethylene-based homopolymers or copolymers such as medium-density polyethylene, low-density polyethylene (for example MARLEX® low-density polyethylene), linear low density polyethylene (for example REXELL®), ionomer, ethylene vinyl acetate (EVA) and/or copolymers thereof, ethylene methacrylate (EMA), ethylene acrylic acid (EAA), ethylene methacrylic acid (EMAA), blends and/or copolymers thereof, or the like, or any other suitable material. Layer 38 may also include a chemical desiccant such as CaO. In some embodiments, layer 38 may be designed to be peelable. In such embodiments, for example, layer 38 may include a blend of one of the above materials with a polybutene resin. Alternatively, layer 38 may include a modified EVA or EMA copolymer. For example, layer 38 may include APPEEL® resin, which is commercially available from DuPont. These are just examples. Other polymers are contemplated including any of those disclosed herein. In some embodiments, layer 38 may include a moisture scavenging material, for example a chemical desiccant, such that layer 38 may be considered a moisture scavenging layer 38. The chemical desiccant may be any suitable material such as calcium oxide, magnesium oxide, barium oxide, barium hydroxide, strontium oxide, aluminum oxide, partially hydrated aluminum oxide, magnesium sulfate, sodium phosphate di-basic, ammonium chloride, potassium carbonate, potassium aluminum disulfate, magnesium chloride, diammonium sulfate, sodium nitrate, calcium chloride, calcium sulfate, sodium chloride, potassium bromide, molecular sieves, clays and blends of these materials.

In examples where calcium oxide is utilized as the desiccant, CaO may combine with oxygen and be converted to Ca(OH)$_2$ according to the following irreversible reaction:

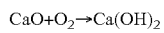

$$CaO+O_2 \rightarrow Ca(OH)_2$$

Thus, in one example, layer 38 may include an AMPACET X101499 film, which may contain about 40 wt-% linear low density polyethylene and 60 wt-% CaO. This may provide suitable desiccation. Embodiments that utilize these materials may be blended with a polybutene resin to provide suitable "peelable" characteristics. Alternatively, layer 38 including a desiccant may also include a modified EVA or EMA copolymer such as APPEEL® resin, which is commercially available from DuPont. These are just examples. Other materials are contemplated.

Layers 40/44/48 may be tie layers that tie or join together adjacent layers. In some embodiments, one or more of layers 40/44/48 may be the same as layer 30. Other embodiments are contemplated, however, where layers 40/44/48 are different from layer 30 and/or one another.

Layer 42 may form a moisture barrier and, thus, include suitable materials so as to form a moisture barrier. For example, layer 42 may include ethylene vinyl alcohol. Other materials, however, are contemplated. Layer 42 may help to further prevent moisture from migrating into layer 38 (and/or other layers).

Layer 46 may include a metal foil such as aluminum foil, which provides a moisture and oxygen barrier. In addition, layer 46 may be substantially opaque such that, collectively, second portion 26 is substantially opaque or otherwise non-transparent.

Layer 50 may be a relatively high-melting outer layer. For example, layer 50 may include polyethylene terephthalate, polyamide, or the like. Layer 50 may provide second portion 26 (and, thus, package 22) protection from exterior abrasion, heat resistance during sealing, as well as a number of additional desirable features.

Sealing medical device 10 within package 22 may generally include disposing medical device within package 22 in which three sides of first portion 24 and second portion 26 of package 22 are sealed together (e.g., heat sealed) so as to form package 22 into a pouch. Additional materials may or may not be added to the package such as, for example, a desiccant and/or oxygen scavenger material that may help manage moisture or oxygen within package 22. After inserting device 10 into package 22, the final side is sealed (e.g., heat sealed). Because first portion 24 is transparent, medical device 10 can be visualized through first portion 24.

It can be appreciated that a number of additional steps may also be performed prior to, during, or after sealing device 10 with package 22. For example, medical device 10 (and/or package 22) may be sterilized using any suitable sterilization procedure such as ethylene oxide sterilization, radiation, steam sterilizing or autoclaving, or the like. Additionally, it may be desirable to modify and/or control the atmosphere within package 22. This may include exposure to nitrogen, oxygen, water (e.g., moisture, humidity, etc.), argon or another inert atmosphere, other atmospheres, or the like. Exposure may include one or more cycles of exposure. If multiple cycles are desired, the cycles may have a vacuum exposure between cycles.

Figure 5:
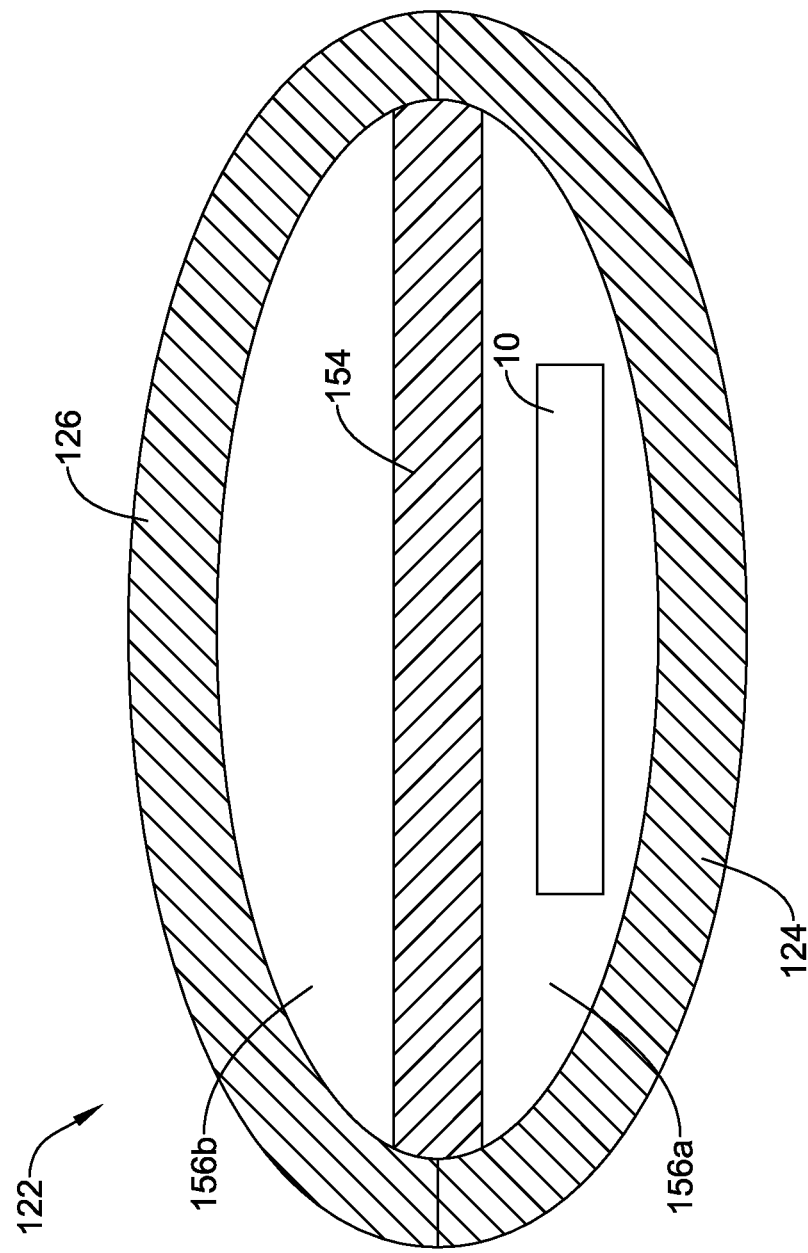
FIG. 5 is a side view of an example medical device shown in FIG. 1 disposed within another example medical device package.

FIG. 5 illustrates another package 122. Package 122 may be similar in form and function to package 22 and it may include first portion 124 and second portion 126. First portion 124 may include a plurality of layers including those listed above for first portion 24. Likewise, second portion 126 may also include a plurality of layers including those listed above for second portion 26. Package 122 may be a "dual-chamber" package or pouch that defines chambers 156a/156b. A layer 154 may be disposed between portions 124/126 to define chambers 156a/156b.

Layer 154 may include a high-density polyethylene (e.g., TYVEK®, commercially available from DuPont), a porous material, coated paper, combinations thereof, and the like, or any other suitable material. Accordingly, layer 154 may be considered "breathable" such that package 122 can be efficiently sterilized via ethylene oxide. For example, medical device 10 may be disposed in one of the chambers (e.g., chamber 156a) of package 122 and sealed (e.g., heat sealed) therein. Thereafter, chamber 156b may be exposed to ethylene oxide, which can pass through layer 154 and gain access to medical device 10 for sterilization. After suitably sterilizing medical device 10, the ethylene oxide can be vented from chamber 156b and chamber 156b can be sealed.

While a number of materials are listed above for use with package 22/122, other polymeric materials are also contemplated. Some examples of suitable polymers include polytetrafluoroethylene (PTFE), ethylene tetrafluoroethylene (ETFE), fluorinated ethylene propylene (FEP), polyoxymethylene (POM), for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate (EVA) and/or copolymers thereof, ethylene methacrylate (EMA), ethylene acrylic acid (EAA), ethylene methacrylic acid (EMAA), silicones, polyethylene (PE), high-density polyethylene (for example MARLEX® high-density polyethylene), medium-density polyethylene, low-density polyethylene (for example MARLEX® low-density polyethylene), linear low density polyethylene (for example REXELL®), ionomer, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like.

EXAMPLES

The invention may be further clarified by reference to the following Example, which serves to exemplify some of the example embodiments, and not to limit the invention in any way.

Example 1

A laminate was made that included a 0.00048 inch thick aluminum oxide (e.g., $AlO_x$) coated polyethylene terephthalate film, a 2-part polyurethane adhesive, and a 0.00060 inch thick LLDPE film. The resultant laminate was designated "Laminate T".

Example 2

A laminate was made that included a 0.00048 inch thick polyethylene terephthalate film, an adhesive (e.g., 2-part polyurethane adhesive), a 0.0015 inch thick polychlorotrifluoroethylene film (e.g., ACLAR® film, commercially available from Honeywell), an adhesive (e.g., 2-part polyurethane adhesive), and a 0.002 inch thick LLDPE film. The resultant laminate was designated "Laminate A".

Example 3

A laminate was made that included a 0.00048 inch thick aluminum oxide (e.g., $AlO_x$) coated polyethylene terephthalate film, a 2-part polyurethane adhesive, another 0.00048 inch thick aluminum oxide (e.g., $AlO_x$) coated polyethylene terephthalate film, and a 0.002 inch thick LLDPE film. The resultant laminate was designated "Laminate M".

Example 4

One packaging pouch was made from Laminate T, one packaging pouch was made using Laminate A, and one packaging pouch was made using Laminate M. Each pouch was sealed along its edges according to modified atmosphere packaging (MAP) conditions with a Sencorp Sealer. The MAP conditions are listed in Table 1.

TABLE 1

MAP Sealing Conditions

| | |
|---|---|
| Number of Cycles: | 4 |
| Seal Temp (upper/lower bar) | 310/110° F. |
| Seal Pressure: | 70 psi |
| Seal Dwell Time | 3 second |
| Vacuum Level: | 5 mbar |
| Vacuum Dwell Time: | 10 second |
| Flushing Gas used: | Nitrogen |
| Flush Level: | 750 psi |
| Flush Dwell Time: | 20 second |
| Ending Flush Level: | 750 psi |
| Ending Flush Dwell Time: | 5 second |
| Ambient Temp.: | 76.5° F. |
| Ambient Relative Humidity: | 42% |

The packaging pouches did not contain a product (e.g., did not contain a medical device) or any foreign material.

The sealed pouches were immediately tested for moisture and oxygen concentration in the packaging pouch headspace using a 3000 Micro GC Headspace Analyzer. The test included disposing the needle of the analyzer into the pouch, withdrawing a sample of gas from the pouch, and analyzing the sample for the presence of oxygen and/or moisture. Because the test is a destructive test, the punctured portion of each package was immediately sealed off after each measurement to prevent any leaking into the packaging pouch headspace. The same packages were then stored at ambient condition and re-tested at different pre-set time periods. The moisture concentration results are listed in Table 2 for the packages made with either Laminate T, Laminate A, or Laminate M.

TABLE 2

Moisture Concentration ($ppm_w$) vs. Time (Day)

| Time (Day) | Laminate T | Laminate A | Laminate M |
|---|---|---|---|
| 0 | 174 | 89 | 140 |
| 14 | 202 | 205 | 440 |
| 33 | 109 | 163 | 315 |
| 62 | 124 | 149 | 605 |
| 92 | 0 | 102 | 167 |
| 126 | 0 | 99 | 166 |
| 152 | 0 | 0 | 150 |

Figure 6:
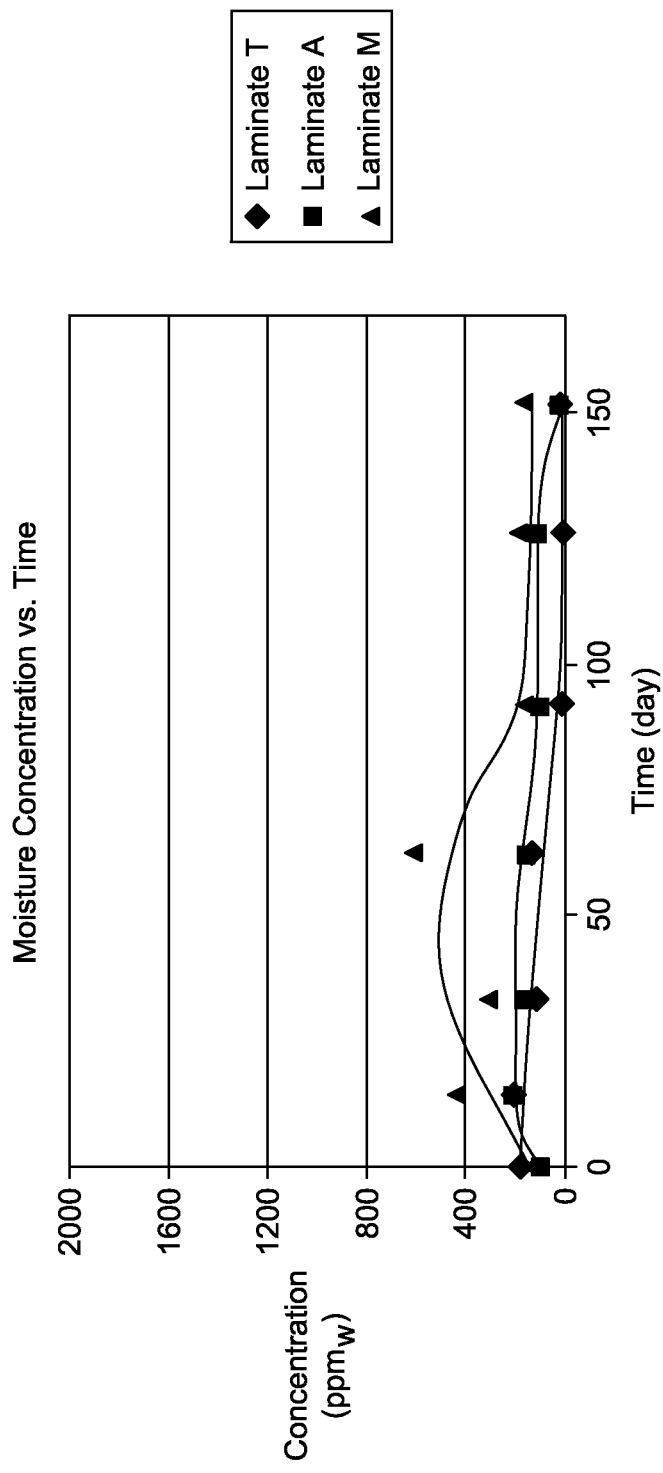
FIG. 6 is a graph illustrating the moisture concentration in example packaging pouches over time.

FIG. 6 is a graphical depiction of the data listed in Table 2. It can be seen in FIG. 6 that the packaging pouch effectively maintained relatively low concentrations of moisture ($H_2O$) in the packaging pouch headspace over a prolonged period of time. In particular, the package made from Laminate T was the greatest barrier to moisture, followed by Laminate A, and then followed by Laminate M.

The oxygen concentration results are listed in Table 3 for the packages made with either Laminate T, Laminate A, or Laminate M.

TABLE 3

Oxygen Concentration ($ppm_w$) vs. Time (Day)

| Time (Day) | Laminate T | Laminate A | Laminate M |
|---|---|---|---|
| 0 | 1267 | 960 | 1335 |
| 14 | 1497 | 1082 | 1405 |
| 33 | 1323 | 1198 | 1451 |
| 62 | 1627 | 1427 | 1355 |
| 92 | 1850 | 1622 | 1573 |
| 126 | 2407 | 2105 | 1705 |
| 152 | 4385 | 3730 | 2158 |

Figure 7:
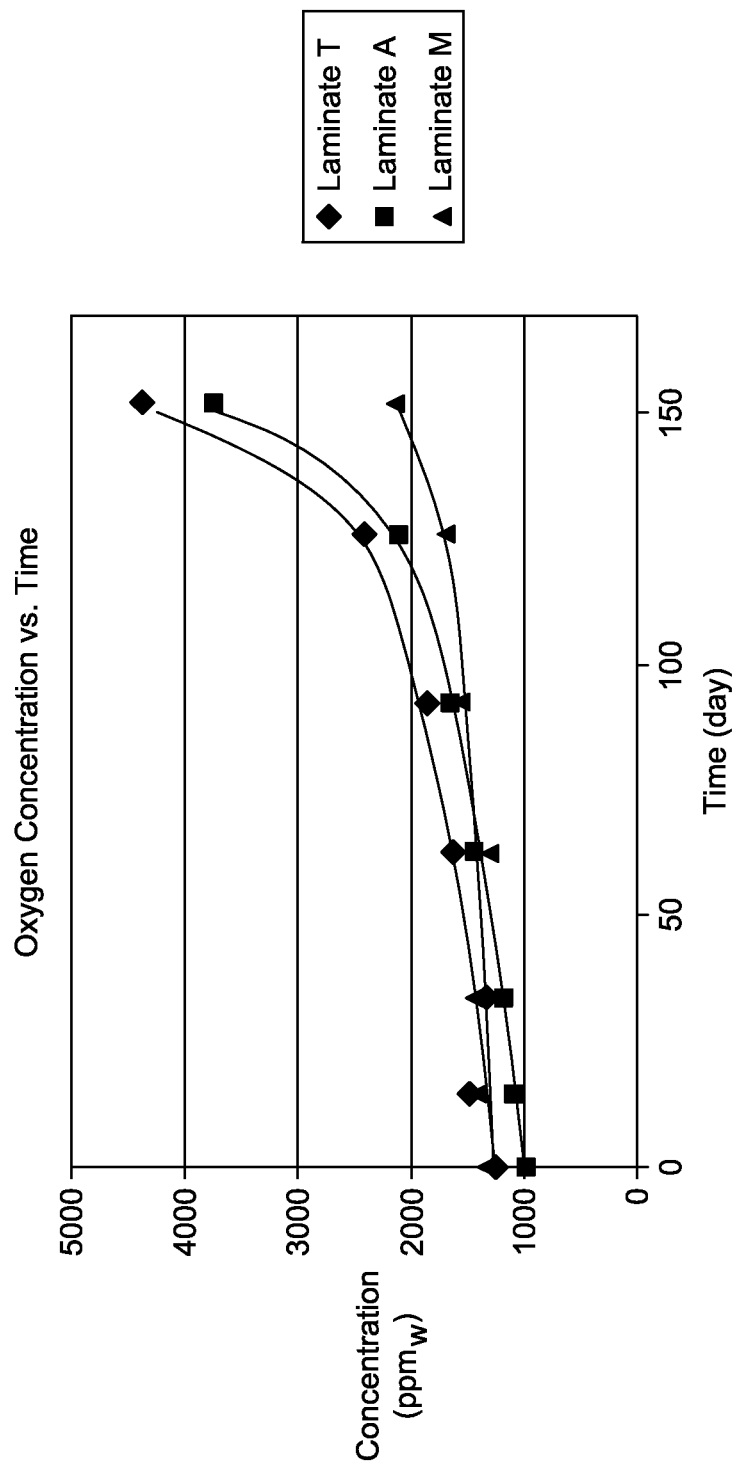
FIG. 7 is a graph illustrating the oxygen concentration in example packaging pouches over time.

FIG. 7 is a graphical depiction of the data listed in Table 3. It can be seen in FIG. 7 that the packaging pouch effectively maintained relatively low concentrations of oxygen ($O_2$) in the packaging pouch headspace over a prolonged period of time. In particular, the package made from Laminate A was the greatest barrier to oxygen, followed by Laminate A, and then followed by Laminate T. In each package, oxygen was maintained at relatively low levels (e.g., less than or equal to about 0.4% ppm, oxygen).

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device packaging assembly, comprising:
   a packaging pouch including a front pouch portion and a back pouch portion;
   wherein the front pouch portion includes a first sheet of material having a plurality of layers;

wherein the back pouch portion includes a second sheet of material having a plurality of layers;
a medical device disposed in the packaging pouch;
wherein the first sheet of material is substantially transparent so that the medical device is viewable through the front pouch portion;
wherein at least one of the plurality of layers of the second sheet of material includes a moisture scavenging layer;
wherein at least one of the plurality of layers of the first sheet of material includes a barrier layer that is configured to maintain the oxygen concentration within the packaging pouch;
wherein the moisture scavenging layer includes an aluminum oxide coated polyethylene terephthalate film;
wherein the barrier layer includes a laminate including a first aluminum oxide coated polyethylene terephthalate film, a polyurethane adhesive, and a second aluminum oxide coated polyethylene terephthalate film; and
wherein at least one of the plurality of layers of the second sheet of material includes a foil layer.

2. The assembly of claim 1, wherein the barrier layer includes a polychlorotrifluoroethylene film.

3. The assembly of claim 1, wherein the barrier layer that is configured to maintain the oxygen concentration within the packaging pouch at 0.4% by weight or less.

4. The assembly of claim 1, wherein the barrier layer that is configured to maintain the oxygen concentration within the packaging pouch at 0.3% by weight or less.

5. The assembly of claim 1, wherein the barrier layer that is configured to maintain the oxygen concentration within the packaging pouch at 0.2% by weight or less.

6. The assembly of claim 1, wherein the packaging pouch is a dual-chamber pouch.

7. A medical device packaging assembly, comprising:
a packaging pouch including a front pouch portion and a back pouch portion;
wherein each of the front pouch portion and the back pouch portion include a plurality of layers;
wherein the front pouch portion includes an oxygen maintaining layer that is configured to maintain the oxygen concentration within the packaging pouch;
wherein the back pouch portion includes a moisture scavenging layer; and
a medical device disposed in the packaging pouch;
wherein the moisture scavenging layer includes an aluminum oxide coated polyethylene film;
wherein the oxygen maintaining layer includes a plurality of aluminum oxide coated polyethylene films;
wherein the moisture scavenging layer is different from the oxygen maintaining layer;
wherein the front pouch portion is substantially transparent so that the medical device is viewable through the front pouch portion.

8. The assembly of claim 7, wherein the moisture scavenging layer includes a laminate including an aluminum oxide coated polyethylene terephthalate film and a linear low density polyethylene film.

9. The assembly of claim 7, wherein the moisture scavenging layer includes a laminate including an aluminum oxide coated polyethylene terephthalate film and a polychlorotrifluoroethylene film.

10. The assembly of claim 7, wherein the oxygen maintaining layer includes a laminate including a first aluminum oxide coated polyethylene terephthalate film, a second aluminum oxide coated polyethylene terephthalate film, and a linear low density polyethylene film.

11. The assembly of claim 7, wherein the oxygen maintaining layer that is configured to maintain the oxygen concentration within the packaging pouch at 0.3% by weight or less.

12. The assembly of claim 7, wherein the oxygen maintaining layer that is configured to maintain the oxygen concentration within the packaging pouch at 0.2% by weight or less.

* * * * *